United States Patent
Ito et al.

(10) Patent No.: US 9,964,492 B2
(45) Date of Patent: *May 8, 2018

(54) SURFACE-ENHANCED RAMAN SCATTERING UNIT AND RAMAN SPECTROSCOPIC ANALYSIS METHOD

(71) Applicant: HAMAMATSU PHOTONICS K.K., Hamamatsu-shi, Shizuoka (JP)

(72) Inventors: Masashi Ito, Hamamatsu (JP); Katsumi Shibayama, Hamamatsu (JP); Kazuto Ofuji, Hamamatsu (JP); Hiroki Oyama, Hamamatsu (JP); Yoshihiro Maruyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 104 days.

This patent is subject to a terminal disclaimer.

(21) Appl. No.: 14/780,776

(22) PCT Filed: Feb. 7, 2014

(86) PCT No.: PCT/JP2014/052927
§ 371 (c)(1),
(2) Date: Sep. 28, 2015

(87) PCT Pub. No.: WO2014/156330
PCT Pub. Date: Oct. 2, 2014

(65) Prior Publication Data
US 2016/0061737 A1    Mar. 3, 2016

(30) Foreign Application Priority Data
Mar. 29, 2013   (JP) ................................. 2013-073444

(51) Int. Cl.
*G01N 21/65*         (2006.01)

(52) U.S. Cl.
CPC .................................. *G01N 21/658* (2013.01)

(58) Field of Classification Search
CPC ............................ G01N 21/658; G01N 21/65
(Continued)

(56) References Cited

U.S. PATENT DOCUMENTS 7,460,224 B2 *  12/2008  Wang ................... G01N 21/648
                                                       356/301
7,483,130 B2    1/2009   Baumberg et al.
(Continued)

FOREIGN PATENT DOCUMENTS

CN          101281133        10/2008
CN          101319994        12/2008
(Continued)

OTHER PUBLICATIONS

K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf; Oct. 6, 2011, XP055289892.
(Continued)

*Primary Examiner* — Hoa Pham
(74) *Attorney, Agent, or Firm* — Drinker Biddle & Reath LLP

(57) ABSTRACT

A surface-enhanced Raman scattering unit comprises a measurement board used upon measurement; a surface-enhanced Raman scattering element, secured to the measurement board, having a substrate and an optical function part, formed on the substrate, for generating surface-enhanced Raman scattering; and a pressing member, secured to the measurement board, having a ring-shaped contact part contacting a peripheral part of the surface-enhanced Raman scattering element and pressing the surface-enhanced Raman scattering element toward the measurement board.

9 Claims, 15 Drawing Sheets

(58) Field of Classification Search
USPC .......................................................... 356/301
See application file for complete search history.

(56) References Cited

U.S. PATENT DOCUMENTS

| | | | |
|---|---|---|---|
| 7,864,313 B2 | | 1/2011 | Baumberg et al. |
| 9,267,894 B2* | | 2/2016 | Ito .................... G01N 21/658 |
| 9,797,842 B2* | | 10/2017 | Tokonami ............ G01N 21/658 |
| 2004/0023046 A1 | | 2/2004 | Schlottig et al. |
| 2006/0034729 A1* | | 2/2006 | Poponin ............... G01N 21/658 422/82.05 |
| 2006/0146323 A1* | | 7/2006 | Bratkovski .......... G01N 21/658 356/301 |
| 2008/0094621 A1 | | 4/2008 | Li et al. |
| 2008/0218761 A1 | | 9/2008 | Nishikawa et al. |
| 2011/0027901 A1* | | 2/2011 | Gaster ............. G01N 33/54373 436/149 |
| 2011/0096157 A1* | | 4/2011 | Fine .................. G02B 21/0008 348/79 |
| 2011/0116089 A1 | | 5/2011 | Schmidt et al. |
| 2011/0166045 A1 | | 7/2011 | Dhawan et al. |
| 2013/0252275 A1 | | 9/2013 | Tokonami et al. |
| 2014/0043605 A1 | | 2/2014 | Tseng et al. |
| 2016/0061736 A1* | | 3/2016 | Ito ........................ G01N 21/658 356/301 |
| 2017/0261435 A1* | | 9/2017 | Oyama ................ G01N 21/658 |

FOREIGN PATENT DOCUMENTS

| | | |
|---|---|---|
| CN | 101672784 | 3/2010 |
| CN | 102282094 | 12/2011 |
| CN | 102472665 | 5/2012 |
| CN | 102483354 | 5/2012 |
| EP | 1 374 989 | 1/2004 |
| JP | H07-260646 A | 10/1995 |
| JP | 2007-538264 A | 12/2007 |
| JP | 2008-519254 | 6/2008 |
| JP | 2008-196992 | 8/2008 |
| JP | 2008-268059 A | 11/2008 |
| JP | 2009-047623 A | 3/2009 |
| JP | 2009-103643 A | 5/2009 |
| JP | 2009-222507 A | 10/2009 |
| JP | 2009-236830 | 10/2009 |
| JP | 2011-021085 | 2/2011 |
| JP | 2011-033518 A | 2/2011 |
| JP | 2011-075348 | 4/2011 |
| JP | 2011-107032 A | 6/2011 |
| JP | 2012-233707 A | 11/2012 |
| JP | 2014-196974 | 10/2014 |
| JP | 2014-025033 | 7/2016 |
| TW | 200728706 | 8/2007 |
| TW | 200932913 | 8/2009 |
| TW | 201111771 | 4/2011 |
| WO | WO-2007/149120 A2 | 12/2007 |
| WO | WO-2012/024006 A2 | 2/2012 |
| WO | WO 2012/077756 | 6/2012 |
| WO | WO 2013/015810 | 1/2013 |
| WO | WO-2014-025034 A1 | 2/2014 |
| WO | WO 2014/156329 | 10/2014 |

OTHER PUBLICATIONS

M. Tomohiko et al., "New localized surface plasmon resonance sensor utilizing nanoimprinting technology", NSTI Nanotechnology Conference and Trade Show-NSTI Nanotech, vol. 1, May 11, 2006, p. 58-61, XP009098538.

W.D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

W. Zhang et al., "Giant and uniform fluorescence enhancement over large areas using plamonic nanodots in 3D resonant cavity nanoantenna by nanoimprinting", Nanotechnology, vol. 23, No. 22, May 10, 2012, p. 225301, XP020224099.

S.M. Wells et al., "Efficient disc on pillar substrates for surface enhanced Raman spectroscopy", Chemical Communications—Chemcom, vol. 47, No. 13, Jan. 1, 2011, p. 3814-3816, XP055289549.

U.S. Office Action dated Oct. 14, 2016 that issued in U.S. Appl. No. 14/420,510 including Double Patenting Rejections on pp. 2-14.

English Machine Translation of JP 2011-107032, Nishikawa et al., Jun. 2, 2011 as attached to U.S. Office Action dated Oct. 14, 2016 in U.S. Appl. No. 14/420,510.

Online, Internet, "Q-SERS™G1 Substrate URL:http://www.optoscience.com/maker/nanova/pdf/Q-SERS_G1.pdf", Opto Science, In., retrieved Mar. 21, 2013.

International Preliminary Report on Patentability dated Oct. 8, 2015 for PCT/JP2014/052927.

International Preliminary Report on Patentability dated Feb. 19, 2015 for PCT/JP2013/071704.

International Preliminary Report on Patentability dated Feb. 19, 2015 for PCT/JP2013/071707.

* cited by examiner

Fig.14
(a)
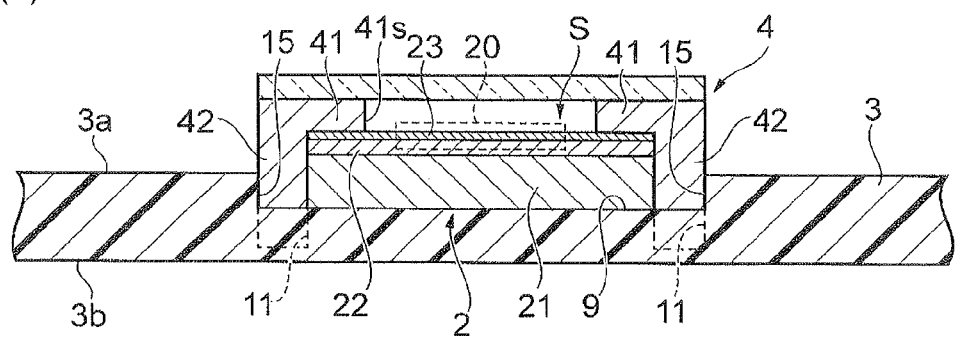
(b)
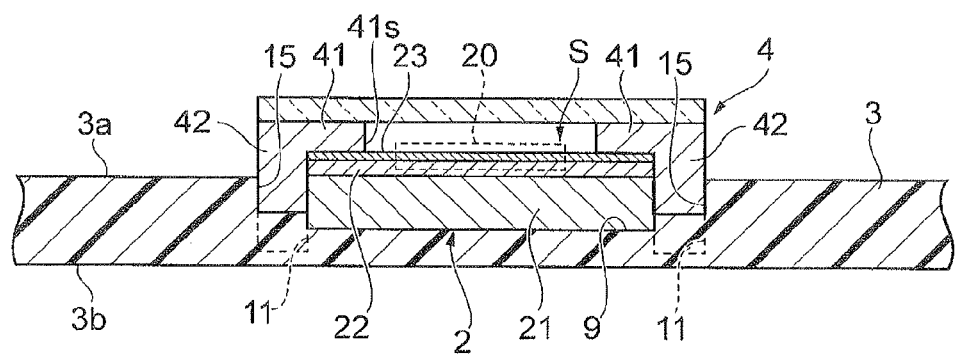

SURFACE-ENHANCED RAMAN SCATTERING UNIT AND RAMAN SPECTROSCOPIC ANALYSIS METHOD

TECHNICAL FIELD

One aspect of the present invention relates to a surface-enhanced Raman scattering unit and a Raman spectroscopic analysis method.

BACKGROUND ART

Known as a conventional surface-enhanced Raman scattering unit is one in which a surface-enhanced Raman scattering element having an optical function part for generating surface-enhanced Raman scattering (SERS) is secured onto a glass slide (see, for example, Non Patent Literature 1).

CITATION LIST

Non Patent Literature

Non Patent Literature 1: "QSERS™ G1 Substrate", [online], Opto Science, Inc., [retrieved on Mar. 21, 2013]. Retrieved from the Internet: <URL: http://www.optoscience.com/maker/nanova/pdf/Q-SERS_G1.pdf>.

SUMMARY OF INVENTION

Technical Problem

When measuring a solution sample by using a surface-enhanced Raman scattering unit such as the one mentioned above, a ring-shaped spacer or the like may be arranged on the glass slide so as to surround the surface-enhanced Raman scattering element and form a space within which the solution sample is placed. In this case, the space formed by the spacer is wider with respect to the optical function part of the surface-enhanced Raman scattering element, so that the solution sample may evaporate and thereby change its concentration or form mist which causes unintentional scattering, thereby adversely affecting the measurement. For suppressing such adverse effects, the space formed by the spacer may be filled with the solution sample, which requires a large amount of the solution sample.

It is therefore an object of one aspect of the present invention to provide a surface-enhanced Raman scattering unit which can suppress adverse effects on the measurement without using a large amount of a sample, and a Raman spectroscopic analysis method using such a surface-enhanced Raman scattering unit.

Solution to Problem

The surface-enhanced Raman scattering in accordance with one aspect of the present invention comprises a measurement board used upon measurement; a surface-enhanced Raman scattering element, secured to the measurement board, having a substrate and an optical function part, formed on the substrate, for generating surface-enhanced Raman scattering; and a pressing member, secured to the measurement board, having a ring-shaped contact part contacting a peripheral part of the surface-enhanced Raman scattering element and pressing the surface-enhanced Raman scattering element toward the measurement board.

In this surface-enhanced Raman scattering unit, the ring-shaped contact part of the pressing member presses the surface-enhanced Raman scattering element toward the measurement board while being in contact with a peripheral part of the surface-enhanced Raman scattering element. Therefore, a space in which the sample can be arranged is restricted by the contact part to a space on the surface-enhanced Raman scattering element excluding the peripheral part. As a consequence, the space can be filled with a relatively small amount of a solution sample. Therefore, this surface-enhanced Raman scattering unit can suppress adverse effects on the measurement without using a large amount of the sample.

In the surface-enhanced Raman scattering unit in accordance with one aspect of the present invention, the pressing member may be mechanically secured to the measurement board. When an adhesive is used for securing the pressing member to the measurement board, for example, deterioration progresses in the optical function part because of ingredients contained in the adhesive when the adhesive cures, during packing and storage, and at the time of measurement. However, the surface-enhanced Raman scattering unit in accordance with one aspect of the present invention uses no adhesive and thus can inhibit the optical function part from deteriorating.

In the surface-enhanced Raman scattering unit in accordance with one aspect of the present invention, the measurement board may have a front face formed with a first depression, the surface-enhanced Raman scattering element and pressing member being contained within the first depression. In this case, the inner side face of the first depression protects the pressing member, thereby favorably holding the space formed by the contact part of the pressing member (the spate in which the sample is arranged).

In the surface-enhanced Raman scattering unit in accordance with one aspect of the present invention, the pressing member may have a top part substantially flush with the front face of the measurement board. In this case, when using a cover at the time of measurement, for example, the cover can stably be supported by the top part of the pressing member and the front face of the measurement board.

In the surface-enhanced Raman scattering unit in accordance with one aspect of the present invention, the contact part may have an inner side face tilted in a tapering manner such that a space defined by the inner side face expands with distance from the surface-enhanced Raman scattering element. In this case, excitation light can be made incident on the surface-enhanced Raman scattering element at a relatively large angle. This can also inhibit stray light from being caused by light scattered at the contact part of the pressing member.

In the surface-enhanced Raman scattering unit in accordance with one aspect of the present invention, the measurement board may be provided with a second depression containing at least a part of the surface-enhanced Raman scattering element on the substrate side and restraining the surface-enhanced Raman scattering element from moving in a direction perpendicular to a thickness direction of the substrate. This can position the surface-enhanced Raman scattering element with respect to the measurement board. This can also prevent the surface-enhanced Raman scattering element from shifting from the measurement board.

In the surface-enhanced Raman scattering unit in accordance with one aspect of the present invention, the measurement board may be integrally formed from a resin. This makes it harder for chipping to occur and thus can securely inhibit the optical function part from being deteriorated by chipped pieces adhering thereto.

In the surface-enhanced Raman scattering unit in accordance with one aspect of the present invention, the measurement board may be provided with a hollowed part so as to form a wall part extending in a direction perpendicular to a thickness direction of the measurement board. This prevents the measurement board from warping and thus can accurately place a focal point of excitation light at the optical function part when arranging the measurement board on a stage of a Raman spectroscopic analyzer in the case where Raman spectroscopic analysis is performed.

The Raman spectroscopic analysis method in accordance with one aspect of the present invention comprises a first step of preparing the above-mentioned surface-enhanced Raman scattering unit and arranging a sample on the optical function part; and a second step, after the first step, of performing Raman spectroscopic analysis by setting the surface-enhanced Raman scattering unit to a Raman spectroscopic analyzer, irradiating the sample arranged on the optical function part with excitation light, and detecting Raman-scattered light derived from the sample.

This Raman spectroscopic analysis method uses the above-mentioned surface-enhanced Raman scattering unit and thus can accurately perform Raman spectroscopic analysis.

Advantageous Effects of Invention

One aspect of the present invention can provide a surface-enhanced Raman scattering unit which can suppress adverse effects on the measurement without using a large amount of a sample, and a Raman spectroscopic analysis method using such a surface-enhanced Raman scattering unit.

BRIEF DESCRIPTION OF DRAWINGS

FIG. 14 is an enlarged sectional view of a modified example of the surface-enhanced Raman scattering unit of FIG. 8.

DESCRIPTION OF EMBODIMENTS

In the following, an embodiment in accordance with one aspect of the present invention will be explained in detail with reference to the drawings. In the explanation of the drawings, the same or equivalent constituents will be referred to with the same signs while omitting their overlapping descriptions.

First Embodiment

Figure 1:
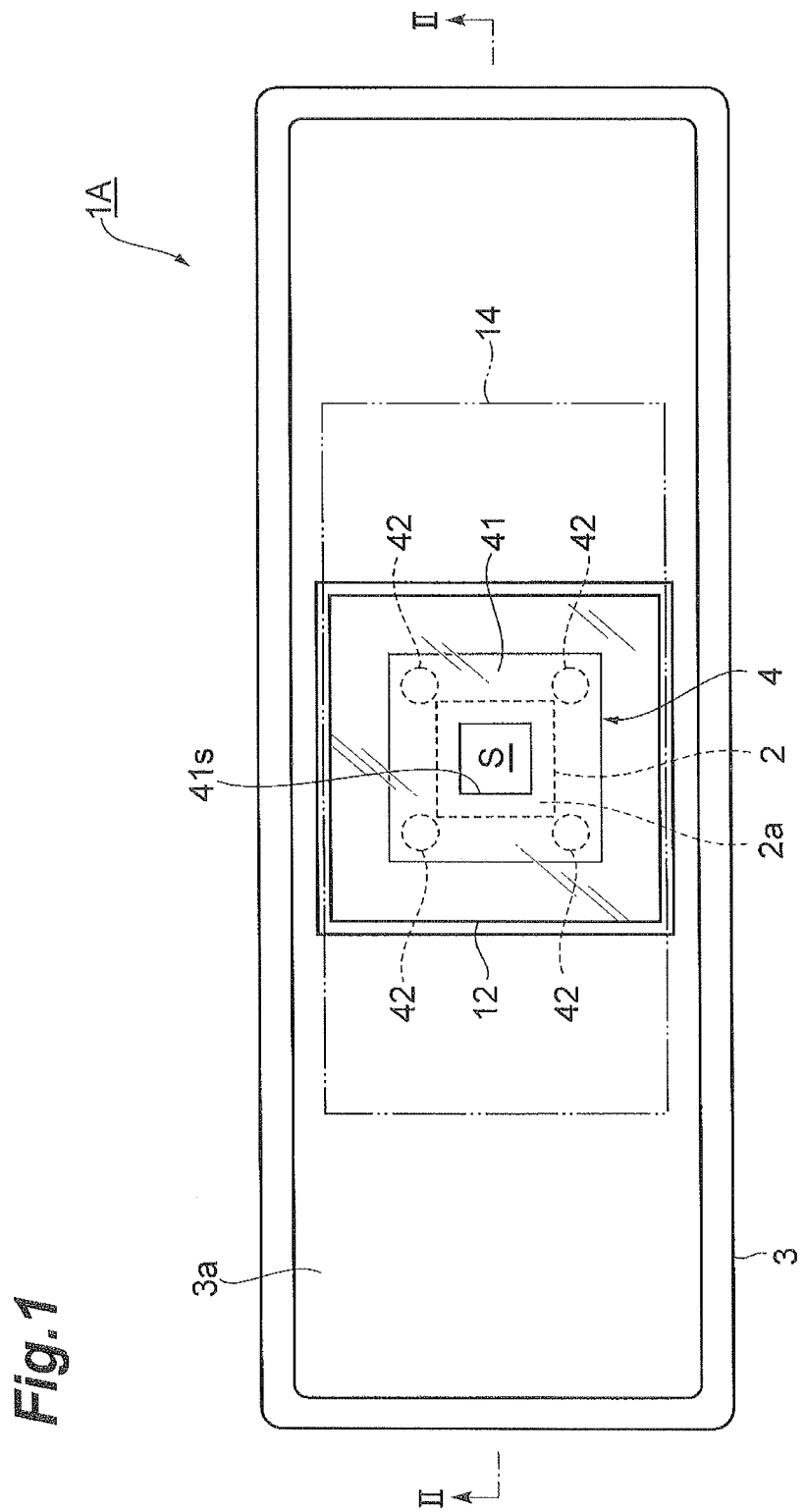
FIG. 1 is a plan view of the surface-enhanced Raman scattering unit of a first embodiment in accordance with one aspect of the present invention.
Figure 2:
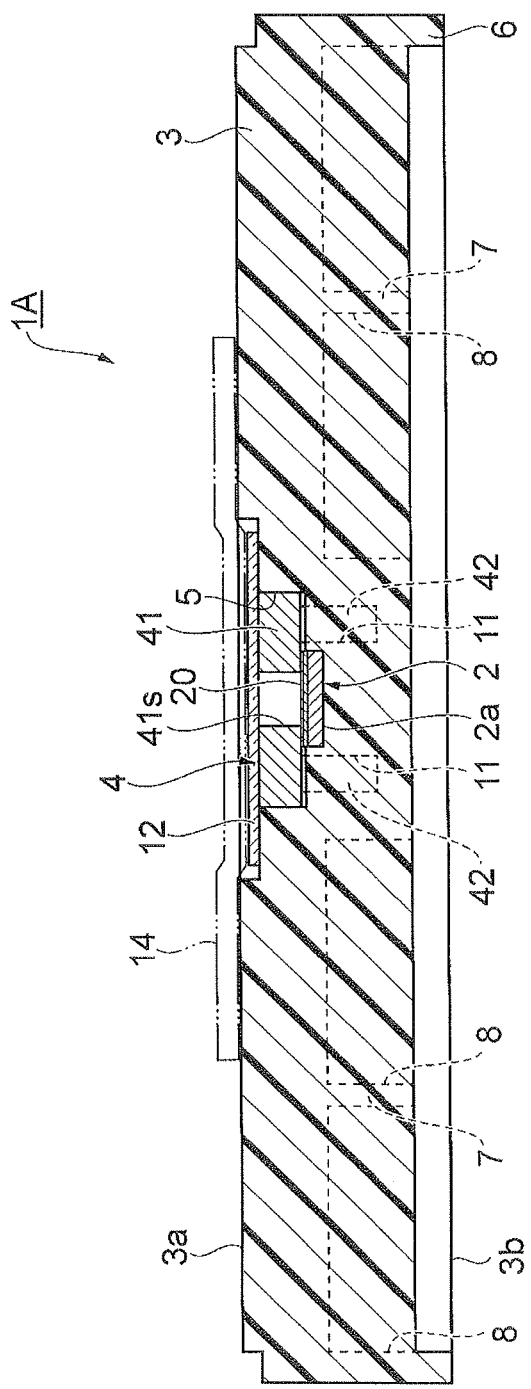
FIG. 2 is a sectional view taken along the line II-II of FIG. 1.

As illustrated in FIGS. 1 and 2, a SERS unit (surface-enhanced Raman scattering unit) 1A comprises a SERS element (surface-enhanced Raman scattering element) 2, a measurement board 3 used when measurement and supporting the SERS element 2, and a pressing member 4 mechanically secured to the measurement board 3. By "mechanically" is meant "through fitting between members without adhesives and the like."

Figure 3:
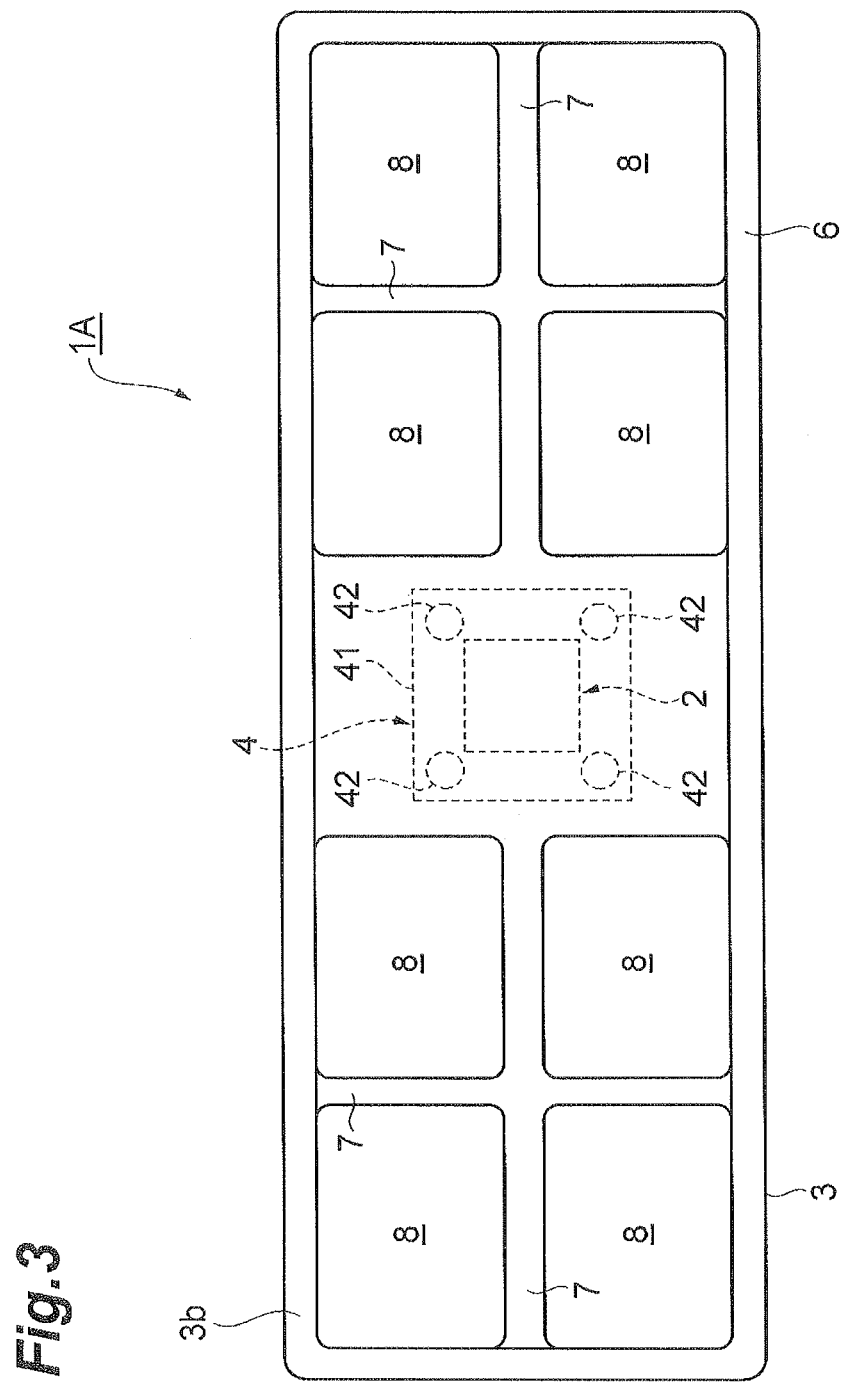
FIG. 3 is a bottom view of the surface-enhanced Raman scattering unit of FIG. 1.

The measurement board 3 has a front face 3a provided with a depression (first depression) 5 containing the SERS element 2 and pressing member 4. On the other hand, as illustrated in FIG. 3, the measurement board 3 has a rear face 3b provided with a plurality of hollowed parts 8 so as to form wall parts 6, 7 extending in directions perpendicular to the thickness direction of the measurement board 3. For example, the wall part 6 is formed like a ring along outer edges of the measurement board 3, while the wall part 7 is formed like grids on the inside of the wall part 6. For example, the measurement board 3 is formed into a rectangular plate. The depression 5 and hollowed parts 8 are formed into rectangular parallelepipeds. The measurement board 3 is integrally formed from materials such as resins (polypropylene, styrol resin, ABS resin, polyethylene, PET, PMMA, silicone, liquid crystal polymer, etc.), ceramics, glass, and silicon by using techniques such as molding, cutting, and etching.

Figure 4:
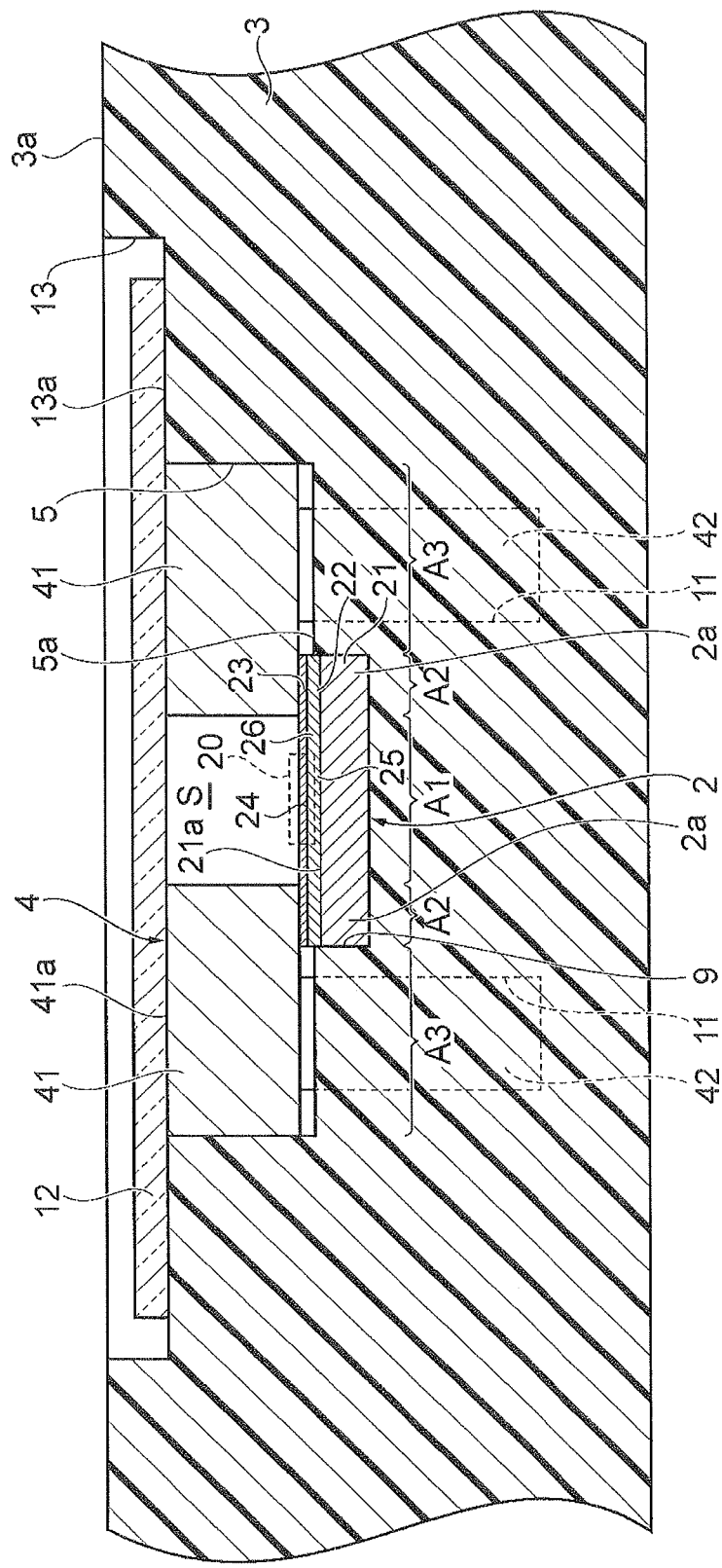
FIG. 4 is an enlarged sectional view taken along the line II-II of FIG. 1.

As illustrated in FIG. 4, the SERS element 2 comprises a substrate 21, a molded layer 22 formed on the substrate 21, and a conductor layer 23 formed on the molded layer 22. For example, the substrate 21 is formed from silicon, glass, or the like into a rectangular plate having an outer form on the order of several hundred μm×several hundred μm to several ten mm×several ten mm and a thickness on the order of 100 μm to 2 mm.

The molded layer 22 has a fine structure part 24, a support part 25, and a frame part 26. The fine structure part 24, which is a region having a periodic pattern, is formed on a surface layer opposite from the substrate 21 at a center part of the molded layer 22. As the periodic pattern, a plurality of pillars each having a thickness and height on the order of several nm to several hundred nm are periodically arranged at a pitch on the order of several ten nm to several hundred nm in the fine structure part 24. The support part 25, which is a region supporting the fine structure part 24, is formed on a front face 21a of the substrate 21. The frame part 26, which is a ring-shaped region surrounding the support part 25, is formed on the front face 21a of the substrate 21.

For example, the fine structure part 24 has a rectangular outer form on the order of several hundred μm×several hundred μm to several ten mm×several ten mm when seen from one side in the thickness direction of the measurement board 3. The support part 25 and frame part 26 have a thickness on the order of several ten nm to several ten μm. The molded layer 22 is integrally formed by molding a resin (examples of which include resins based on acrylics, fluorine, epoxy, silicone, and urethane, PET, polycarbonate, and inorganic/organic hybrid materials) or low-melting glass arranged on the substrate 21 by nanoimprinting, for example.

The conductor layer 23 is formed over the fine structure part 24 to the frame part 26. In the fine structure part 24, the conductor layer 23 reaches a surface of the support part 25 which is exposed to the side opposite from the substrate 21. For example, the conductor layer 23 has a thickness on the order of several nm to several μm. The conductor layer 23 is formed by vapor-depositing a conductor such as a metal (Au, Ag, Al, Cu, Pt, or the like) on the molded layer 22 molded by nanoimprinting, for example.

Figure 5:
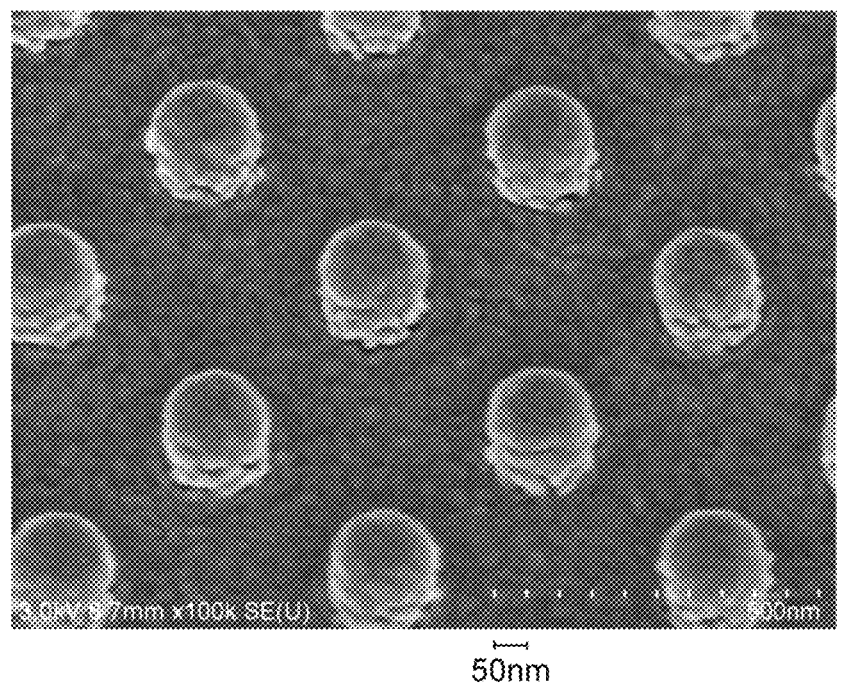
FIG. 5 is a SEM photograph of an optical function part in the surface-enhanced Raman scattering unit of FIG. 1.

In the SERS element 2, the conductor layer 23 formed over the front face of the fine structure part 24 and the surface of the support part 25 exposed to the side opposite from the substrate 21 produces an optical function part 20, which generates surface-enhanced Raman scattering, on the substrate 21. For reference, a SEM photograph of the optical function part 20 is illustrated. The optical function part illustrated in FIG. 5 is one in which Au is vapor-deposited as a conductor layer so as to have a thickness of 50 nm on a fine structure part made of a nanoimprint resin having a plurality of pillars (each having a diameter of 120 nm and a height of 180 nm) periodically arranged at a predetermined pitch (a distance of 360 nm between center lines).

As illustrated in FIG. 4, the depression 5 has a bottom face 5a provided with a depression (second depression) 9 containing a part of the SERS element 2 on the substrate 21 side. The depression 9 is formed complementary to a part of the SERS element 2 on the substrate 21 side and restrains the SERS element 2 from moving in directions perpendicular to the thickness direction of the substrate 21. The SERS element 2 is secured to the measurement board 3 by a given method. For example, the SERS element 2 may be secured to the inner surface of the depression 9 with an adhesive or held between a contact part 41 of the pressing member 4 which will be explained later and the bottom face of the depression 9 so as to be secured.

Here, the measurement board 3 includes a first region A1 located at substantially the center of the measurement board 3 when seen in the thickness direction of the measurement board 3, a ring-shaped second region A2 surrounding the first region A1, and a ring-shaped third region A3 further surrounding the second region A2. The depression 5 is disposed over the first to third regions A1 to A3, while the depression 9 is formed in the first and second regions A1, A2. Therefore, the SERS element 2 is located on the first and second regions A1, A2, while the optical function part 20 is located on the first region A1.

The pressing member 4 is formed into a ring when seen in the thickness direction of the substrate 21 and has the contact part 41 having a thickness in the thickness direction of the substrate 21 and leg parts 42 respectively extending from four corners of the contact part 41 toward the rear face 3b of the measurement board 3. The contact part 41 is arranged on the second and third regions A2, A3 and in contact with the upper face of a peripheral part 2a of the SERS element 2 (conductor layer 23) on the second region A2. Therefore, when seen in the thickness direction of the substrate 21, the contact part 41 surrounds the optical function part 20 located on the first region A1.

As a consequence, an inner side face 41s of the contact part 41 and the front face of the SERS element 2 (the surface layer of the conductor layer 23) form a space S on the SERS element 2. This space S can be used as a cell (chamber) in which a sample (e.g., a solution sample) is arranged at the time of measurement. Here, the contact part 41 rides on the peripheral part 2a of the SERS element 2 on the second region A2 so as to surround the optical function part 20, whereby the space in which the sample can be arranged at the time of measurement is restricted to the space S on the SERS element 2 excluding the peripheral part 2a (i.e., the space on the first region A1). That is, the contact part 41 functions as restriction means for restricting the space in which the sample can be arranged at the time of measurement. Here, since the inner side face 41s of the contact part 41 extends along the thickness direction of the substrate 21, the space S has a rectangular form when seen in a direction perpendicular to the thickness direction of the substrate 21.

Fitting holes 11 are formed in the bottom face 5a of the depression 5 so as to correspond to the leg parts 42, respectively. The leg parts 42 are fitted into their corresponding fitting holes 11 in a state where the contact part 41 surrounds the optical function part 20 and is in contact with the conductor layer 23 in the peripheral part 2a of the SERS element 2. Thus, the pressing member 4 formed separately from the measurement board 3 is mechanically secured to the measurement board 3, while the SERS element 2 (the peripheral part 2a of the SERS element 2) arranged in the depression 9 is pressed (under pressure) by being held between the measurement board 3 and the contact part 41 of the pressing member 4. The fitting holes 11 do not penetrate through the measurement board 3 but are bottomed.

For example, the contact part 41 is formed such that its outer and inner edges form rectangles (i.e., a rectangular ring as a whole) when seen in the thickness direction of the substrate 21. Forming the contact part 41 into a rectangular ring can produce the space S while making the contact part 41 have substantially a constant width when seen in the thickness direction of the substrate 21. By way of another example, the contact part 41 may be formed such as to have a rectangular outer edge and a circular inner edge when seen in the thickness direction of the substrate 21. Making the inner edge of the contact part 41 circular prevents pressures from acting locally on the SERS element 2. The leg parts 42 and fitting holes 11 are formed cylindrical. The pressing member 4 having the contact part 41 and leg parts 42 is integrally formed from materials such as resins (polypropylene, styrol resin, ABS resin, polyethylene, PET, PMMA, silicone, liquid crystal polymer, etc.), ceramics, glass, and silicon by using techniques such as molding, cutting, and etching.

The SERS unit 1A further comprises a cover 12 which transmits light therethrough. The cover 12 is arranged at a widened part 13 provided in an opening part of the depression 5 and covers the opening part of the depression 5. The widened part 13 is formed complementary to the cover 12 and restrains the cover 12 from moving in directions perpendicular to the thickness direction of the cover 12. The contact part 41 of the pressing member 4 has a front face 41a substantially flush with a bottom face 13a of the widened part 13. As a consequence, the cover 12 is supported not only by the measurement board 3 but also by the pressing member 4. For example, the cover 12 is formed from glass or the like into a rectangular plate having an outer form on the order of 18 mm×18 mm and a thickness on the order of 0.15 mm. Until the SERS unit 1A is used, a temporary securing film 14 is attached to the measurement board 3 so as to overlie the cover 12, whereby the cover 12 is prevented from dropping out of the measurement board 3.

Figure 6:
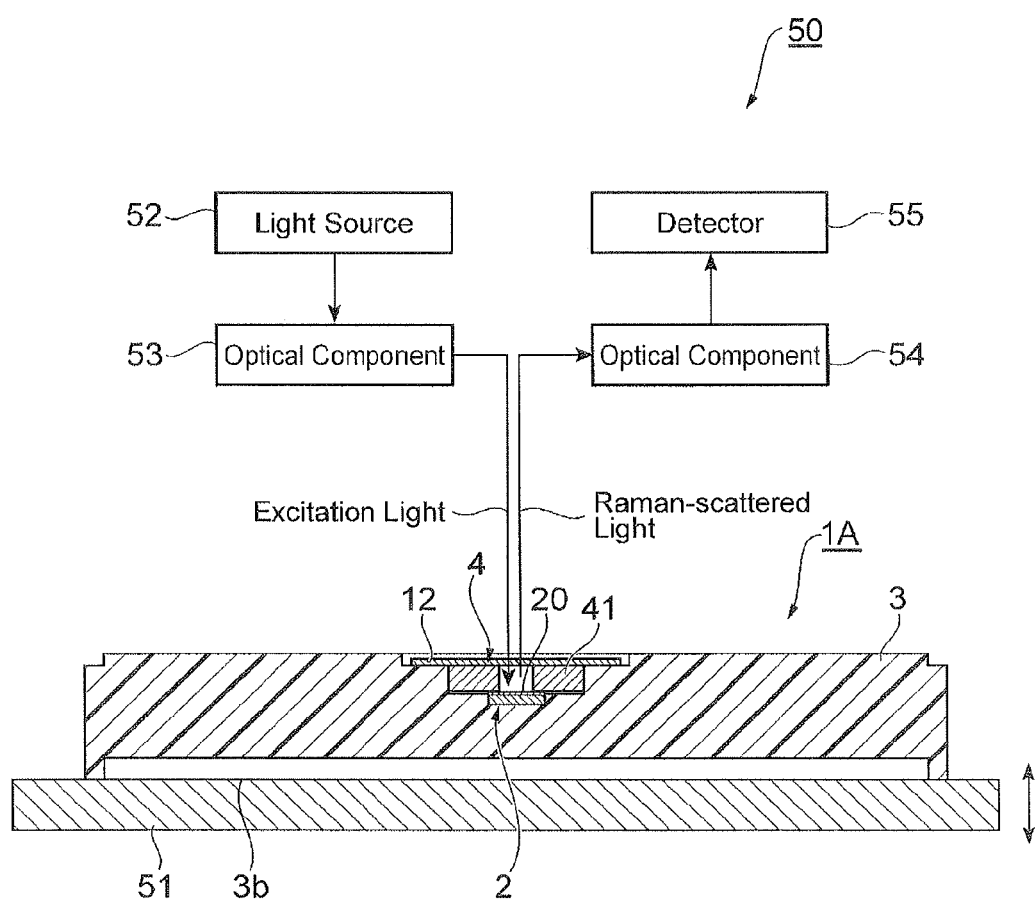
FIG. 6 is a structural diagram of a Raman spectroscopic analyzer to which the surface-enhanced Raman scattering unit of FIG. 1 is set.

A Raman spectroscopic analysis method using the SERS unit 1A will now be explained. Here, as illustrated in FIG. 6, the Raman spectroscopic analysis method is performed in a Raman spectroscopic analyzer 50 comprising a stage 51 for supporting the SERS unit 1A, a light source 52 for emitting excitation light, an optical component 53 for effecting collimation, filtering, condensing, and the like necessary for irradiating the optical function part 20 with the excitation light, an optical component 54 for effecting collimation, filtering, and the like necessary for guiding Raman-scattered light to a detector 55, and the detector 55 for detecting the Raman-scattered light.

First, the SERS unit 1A is prepared, the temporary securing film 14 is peeled off from the measurement board 3, and the cover 12 is removed from the measurement board 3. Then, a solution sample (or a dispersion of a powder sample in water or in a solution of ethanol) is dropped to the space S formed (as restricted) by the contact part 41 of the pressing member 4, so as to be arranged on the optical function part 20 (first step). Here, for example, the solution sample can be arranged on the optical function part 20 by filling the space S therewith.

Subsequently, for reducing the lens effect, the cover 12 is arranged on the widened part 13 of the measurement board 3, so as to come into close contact with the solution sample.

Thereafter, the measurement board 3 is arranged on the stage 51, and the SERS unit 1A is set to the Raman spectroscopic analyzer 50. Subsequently, the solution sample arranged on the optical function part 20 is irradiated with the excitation light emitted through the optical component 53 from the light source 52. At this time, the stage 51 is moved such that a focal point of the excitation light is located at the optical function part 20. This causes surface-enhanced Raman scattering at the interface between the optical function part 20 and the solution sample, whereby Raman-scattered light derived from the solution sample is released after being enhanced by about $10^8$ times, for example. Then Raman spectroscopic analysis is performed by detecting the released Raman-scattered light by the detector 55 through the optical component 54 (second step).

Not only the above-mentioned method but the following methods may also be used for arranging the sample on the optical function part 20. For example, the measurement board 3 may be held, so as to dip the SERS element 2 into a solution sample (or a dispersion of a powder sample in water or in a solution of ethanol or the like), lift it up, and then blow it to dry. A minute amount of a solution sample (or a dispersion of a powder sample in water or in a solution of ethanol or the like) may be dropped on the optical function part 20 and left to dry. A powder sample may be dispersed as it is on the optical function part 20.

Effects exhibited by the SERS unit 1A will now be explained. In the SERS unit 1A, the ring-shaped contact part 41 of the pressing member 4 presses the SERS element 2 toward the measurement board 3 while being in contact with the peripheral part 2a of the SERS element 2. Therefore, the space in which the sample can be arranged is restricted by the contact part 41 to the space S on the SERS element 2 excluding the peripheral part 2a. This makes it possible for the space S to be filled with a relatively small amount of a solution sample. As a consequence, the SERS unit 1A can suppress adverse effects on measurement without using a large amount of the sample.

Since the space in which the sample can be arranged is restricted (to the space S) by the contact part 41 of the pressing member 4, solution samples dropped on the optical function part 20 and powder samples dispersed on the optical function part 20 are inhibited from being arranged in areas other than the optical function part 20 in the SERS unit 1A.

In the SERS unit 1A, the pressing member 4 is mechanically secured to the measurement board 3. Therefore, as compared with a case using an adhesive for securing the pressing member 4 with respect to the measurement board 3, for example, the optical function part 20 is inhibited from being deteriorated by ingredients contained in the adhesive. In the SERS unit 1A, the ring-shaped contact part 41 presses the peripheral part 2a of the SERS element 2 while being in contact with the peripheral part 2a. Therefore, even when the space S formed by the contact part 41 is filled with a solution sample, the latter is less likely to leak out of the space S. As a consequence, even if an adhesive is used for securing the pressing member 4 and the measurement board 3 to each other and the SERS element 2 and the measurement board 3 to each other, the adhesive will be relatively less influential.

In the SERS unit 1A, the contact part 41 of the pressing member 4 presses the SERS element 2 toward the measurement board 3. This can hold the SERS element 2 securely in the measurement board 3. This can also prevent the molded layer 22 and conductor layer 23 formed on the substrate 21 in the SERS element 2 from peeling from the substrate 21.

In the SERS unit 1A, the measurement board 3 is formed with the depression 5 for containing the SERS element 2 and pressing member 4. Therefore, the inner side face of the depression 5 protects the outer side face of the contact part 41 of the pressing member 4, whereby the space S formed by the contact part 41 is held favorably.

In the SERS unit 1A, the measurement board 3 (the bottom face 5a of the depression 5) is provided with the depression 9 containing a part of the SERS element 2 on the substrate 21 side and restraining the SERS element 2 from moving in directions perpendicular to the thickness direction of the substrate 21. This can position the SERS element 2 with respect to the measurement board 3. This can also prevent the SERS element 2 from shifting from the measurement board 3.

In the SERS unit 1A, the measurement board 3 is integrally formed from a resin. This makes it harder for chipping to occur and thus can securely inhibit the optical function part 20 from being deteriorated by chipped pieces adhering thereto. Further, embossing the outer surface of the measurement board 3 or using a resin having a light-absorbing color as a material for the measurement board 3 can inhibit stray light from occurring at the time of Raman spectroscopic analysis.

In the SERS unit 1A, the measurement board 3 is provided with a plurality of hollowed parts 8 so as to form the wall parts 6, 7 extending in directions perpendicular to the thickness direction of the measurement board 3. This prevents the measurement board 3 from warping and thus can accurately place a focal point of excitation light at the optical function part 20 when arranging the measurement board 3 on the stage 51 of the Raman spectroscopic analyzer 50 in the case where Raman spectroscopic analysis is performed.

Even if a solution sample leaks out into a region on the outside of the space S formed by the contact part 41, the bottomed fitting holes 11 provided in the bottom face 5a of the depression 5 in the measurement board 3 will prevent the solution sample from leaking out of the depression 5.

Figure 7:
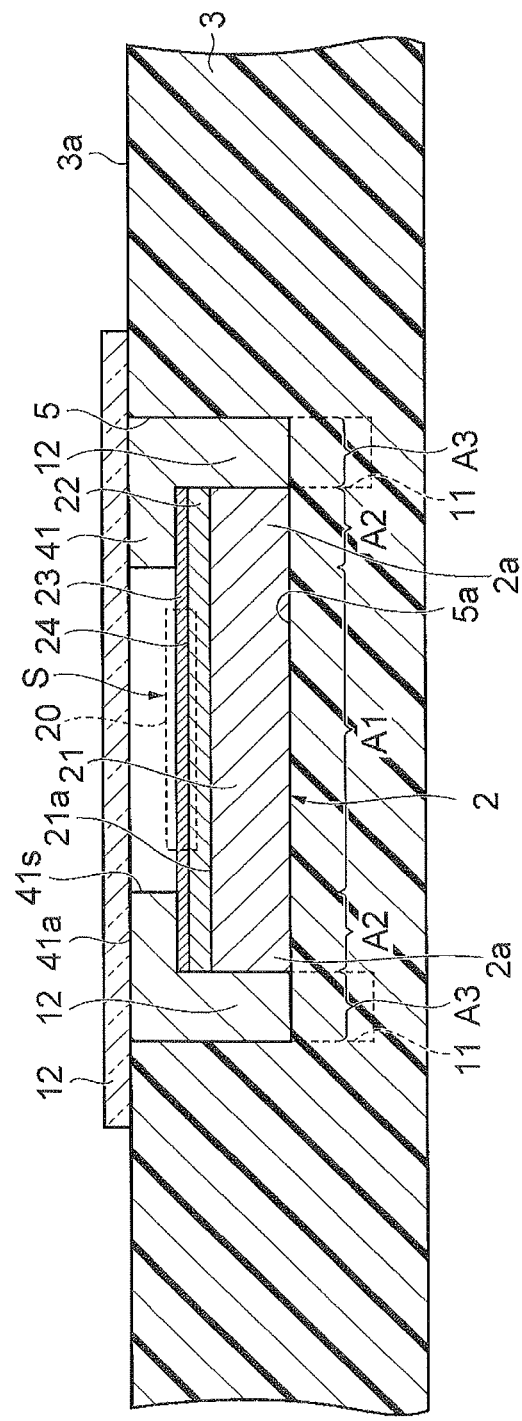
FIG. 7 is an enlarged sectional view of a modified example of the surface-enhanced Raman scattering unit of FIG. 1.

A modified example of the SERS unit 1A will now be explained. In the SERS unit 1A, as illustrated in FIG. 7, the front face 3a of the measurement board 3 may be provided with the depression 5, while the bottom face 5a of the depression 5 is devoid of the depression 9. In this case, the SERS element 2 and pressing member 4 are contained in the depression 5, while the SERS element 2 is arranged on the bottom face 5a of the depression 5. The top part of the pressing member 4 (the front face 41a of the contact part 41) is substantially flush with the front face 3a of the measurement board 3.

This structure also makes the inner side face of the depression 5 protect the outer side face of the contact part 41 of the pressing member 4, thereby favorably holding the space S formed by the contact part 41. This also enables the top part of the pressing member 4 (the front face 41a of the contact part 41) and the front face 3a of the measurement board 3 to hold the cover 12 stably therebetween.

Second Embodiment

Figure 8:
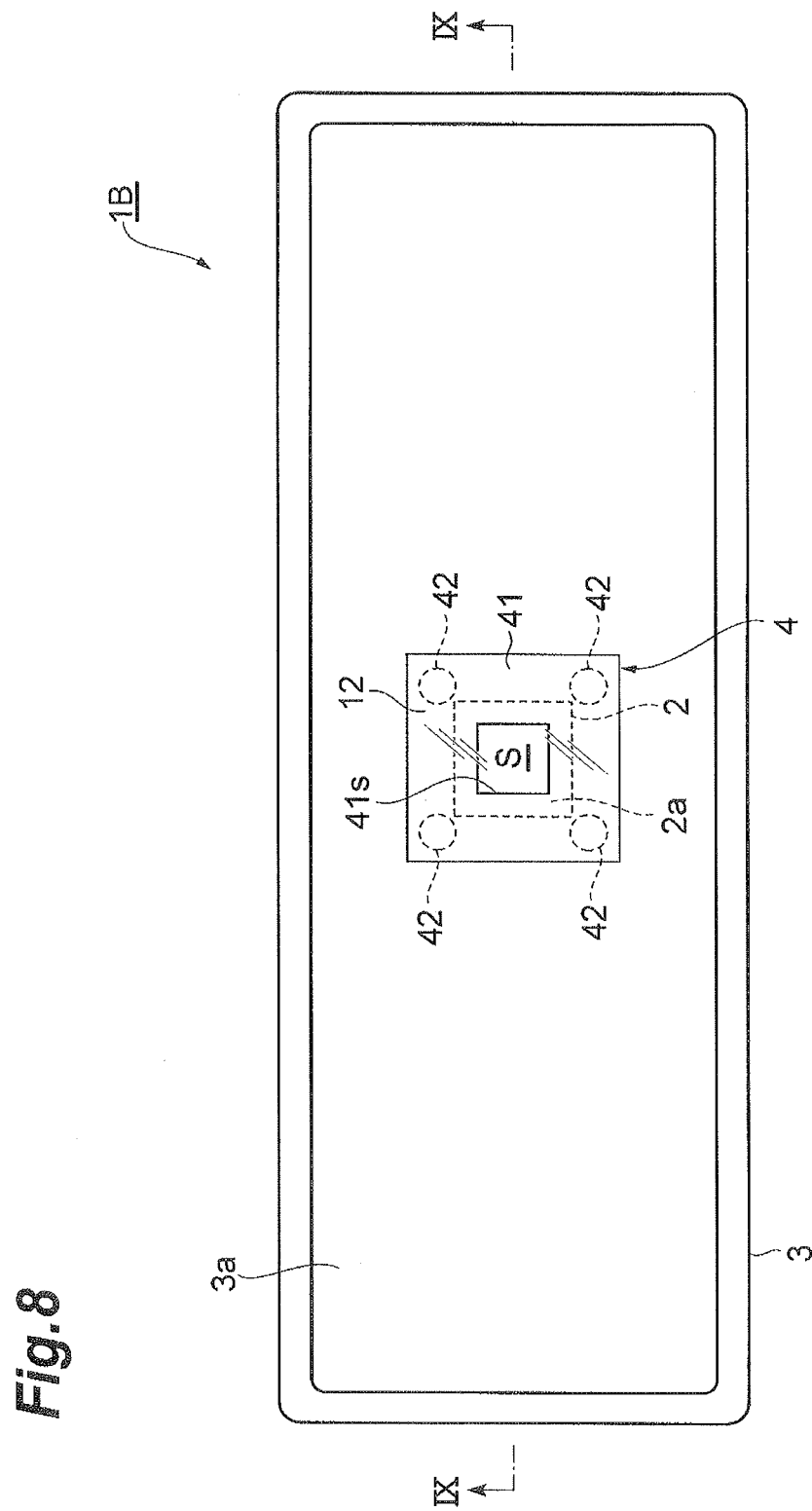
FIG. 8 is a plan view of the surface-enhanced Raman scattering unit of a second embodiment in accordance with one aspect of the present invention.
Figure 9:
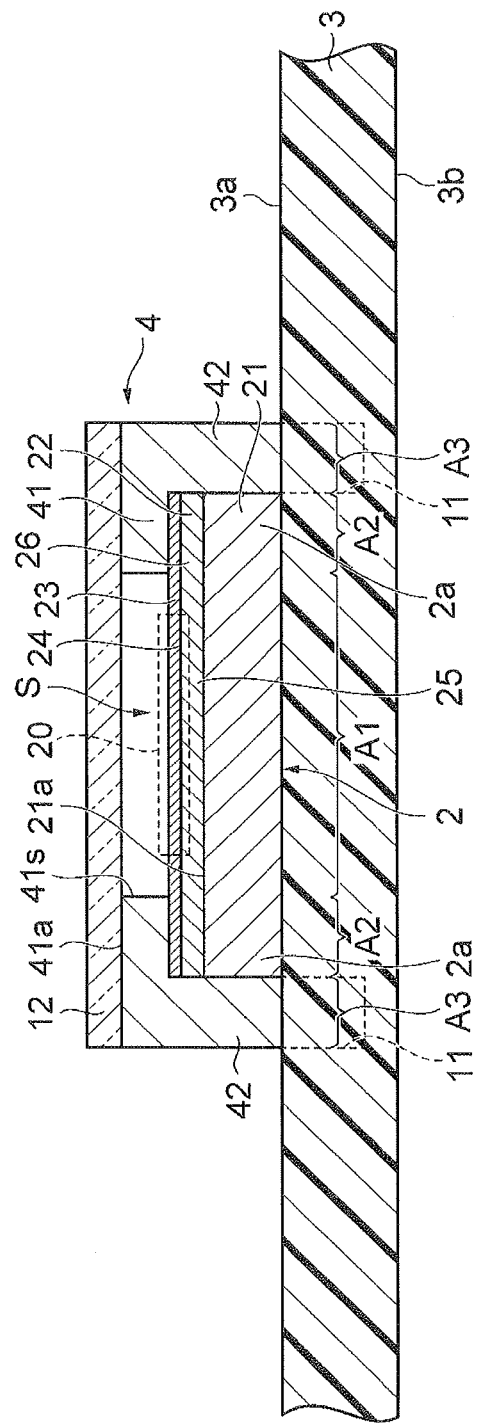
FIG. 9 is an enlarged sectional view taken along the line IX-IX of FIG. 8.

As illustrated in FIGS. 8 and 9, a SERS unit 1B differs from the above-mentioned SERS unit 1A in that the measurement board 3 is devoid of the depression 5 (and depression 9). In the SERS unit 1B, the SERS element 2 is arranged on the front face 3a of the measurement board 3 and secured to the measurement board 3 (the lower face of the substrate 21 of the SERS element 2 abuts against the front face 3a of the measurement board 3). The fitting holes 11 are formed in the front face 3a of the measurement board 3 so as to correspond to the respective leg parts 42. The leg parts 42 are fitted into their corresponding fitting holes 11 in a state where the contact part 41 surrounds the optical function part 20 and is in contact with the conductor layer 23 in the peripheral part 2a of the SERS element 2.

That is, the pressing member 4 is mechanically secured to the measurement board 3, while the SERS element 2 (the peripheral part 2a of the SERS element 2) arranged on the front face 3a of the measurement board 3 is pressed (under pressure) by being held between the measurement board 3 and the contact part 41 of the pressing member 4 also in the SERS unit 1B. The fitting holes 11 do not penetrate through the measurement board 3 and are bottomed in this case as well. The cover 12 has substantially the same outer form as that of the contact part 41 of the pressing member 4 when seen in the thickness direction of the substrate 21 and is supported by the front face 41a of the contact part 41 (the top part of the pressing member 4) alone.

In the SERS unit 1B constructed as in the foregoing, the ring-shaped contact part 41 of the pressing member 4 presses the SERS element 2 toward the measurement board 3 while being in contact with the peripheral part 2a of the SERS element 2 as in the above-mentioned SERS unit 1A. Therefore, the space in which a sample can be arranged is restricted by the contact part 41 to the space S on the SERS element 2 excluding the peripheral part 2a. This makes it possible for the space S to be filled with a relatively small amount of a solution sample. As a consequence, the SERS unit 1B can also suppress adverse effects on measurement without using a large amount of the sample.

In the SERS unit 1B, the SERS element 2 is arranged on the front face 3a of the measurement board 3, while the measurement board 3 is devoid of the depression 5. This can inhibit the measurement board 3 from lowering its strength. The measurement board 3 is not provided with a space (such as the depression 5) for containing the SERS element 2 and pressing member 4 and thus can be constructed relatively thin, so as to cut down the cost of materials.

Figure 10:
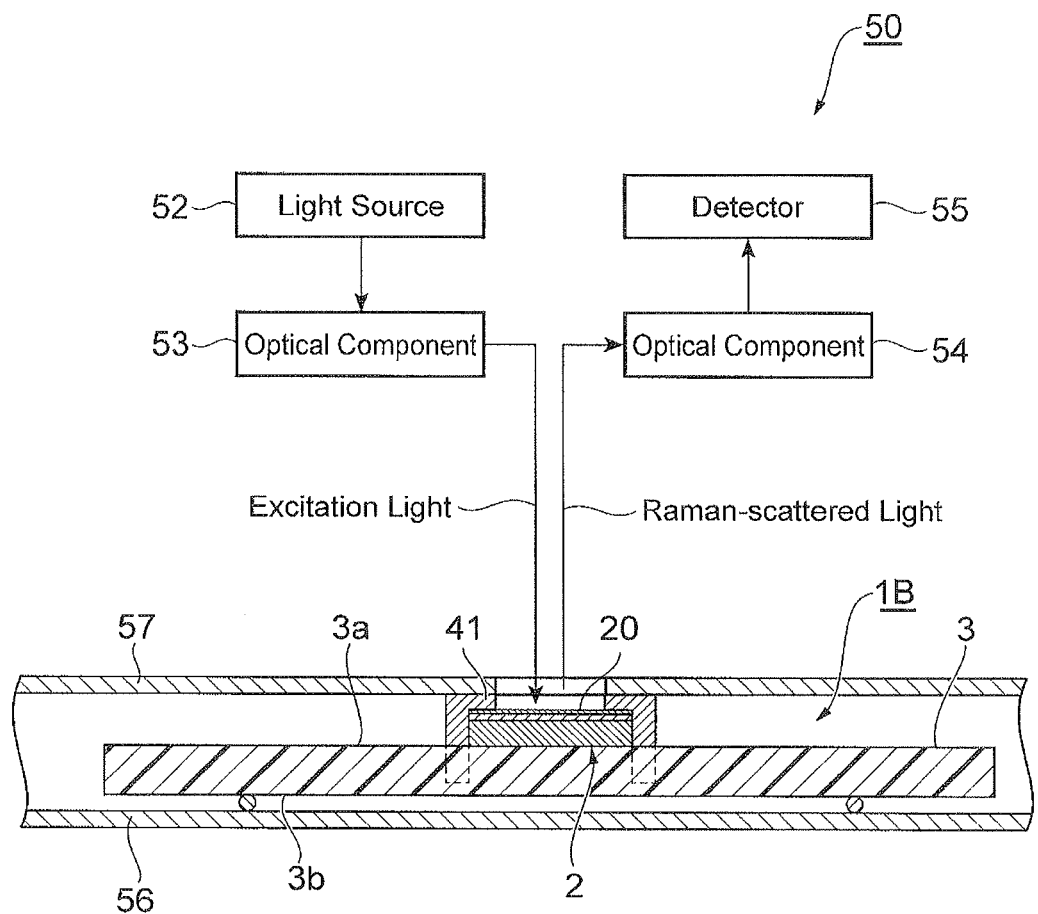
FIG. 10 is a structural diagram of a Raman spectroscopic analyzer to which the surface-enhanced Raman scattering unit of FIG. 8 is set.

In the case where Raman spectroscopic analysis is performed in the SERS unit 1B, as illustrated in FIG. 10, the contact part 41 can be utilized as a spacer for locating a focal point of excitation light at the optical function part 20 when setting the SERS unit 1B to a pressing mechanism 56 of the Raman spectroscopic analyzer 50 so that the contact part 41 abuts against a holder 57 of the Raman spectroscopic analyzer 50. At this time, the contact part 41 prevents the optical function part 20 from being damaged by physical contact.

Figure 11:
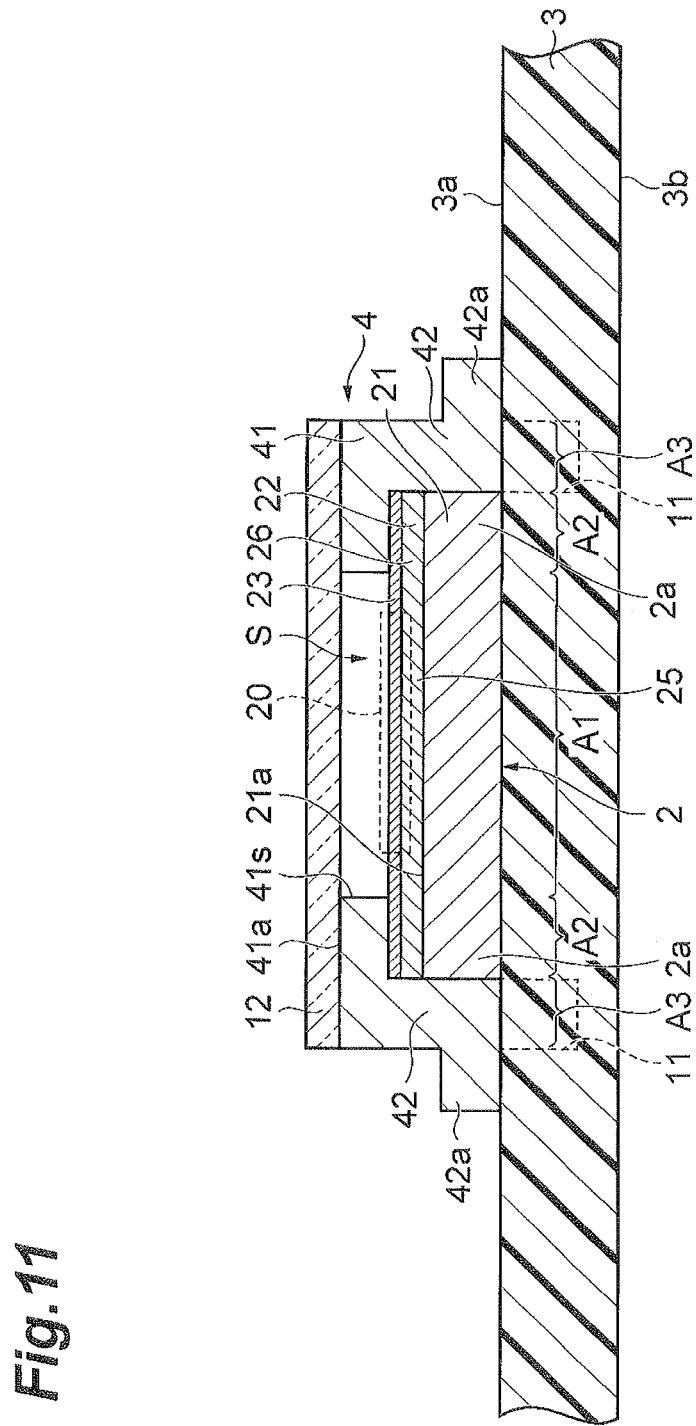
FIG. 11 is an enlarged sectional view of a modified example of the surface-enhanced Raman scattering unit of FIG. 8.

A modified example of the SERS unit 1B will now be explained. As illustrated in FIG. 11, stoppers 42a may be formed for the respective leg parts 42 of the pressing member 4 in the SERS unit 1B. This structure enables the leg parts 42 to be fitted into the fitting holes 11 until the stoppers 42a come into contact with the measurement board 3, so that substantially a fixed pressure acts on the SERS element 2 as the contact part 41 comes into contact therewith, thereby preventing the pressure from acting on the SERS element 2 more than necessary.

Figure 12:
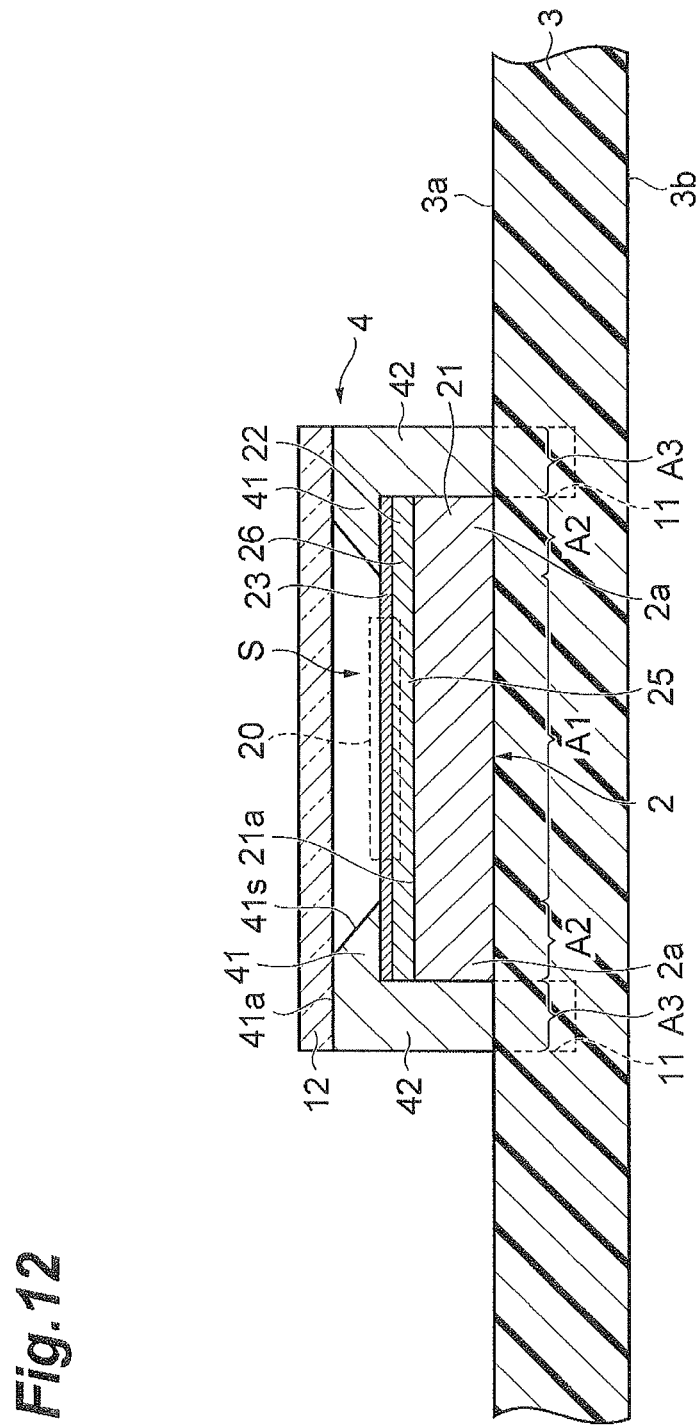
FIG. 12 is an enlarged sectional view of a modified example of the surface-enhanced Raman scattering unit of FIG. 8.

In the SERS unit 1B, as illustrated in FIG. 12, the inner side face 41s of the contact part 41 of the pressing member 4 may be tilted in a tapering manner such that the space S defined (formed) by the inner side face 41s expands with distance from the SERS element 2. In this case, the space S is trapezoidal when seen in a direction perpendicular to the thickness direction of the substrate 21 by the contact part 41. In this structure, excitation light can be made incident on the SERS element 2 at a relatively large angle in Raman spectroscopic analysis. This can also inhibit stray light from being caused by light scattered at the contact part 41 of the pressing member 4.

The foregoing embodiment explains one embodiment in accordance with one aspect of the present invention. Therefore, the one aspect of the present invention is not limited to the above-mentioned embodiment. The one aspect of the present invention may arbitrarily modify the above-mentioned embodiment within a scope not departing from the gist of each claim.

Figure 13:
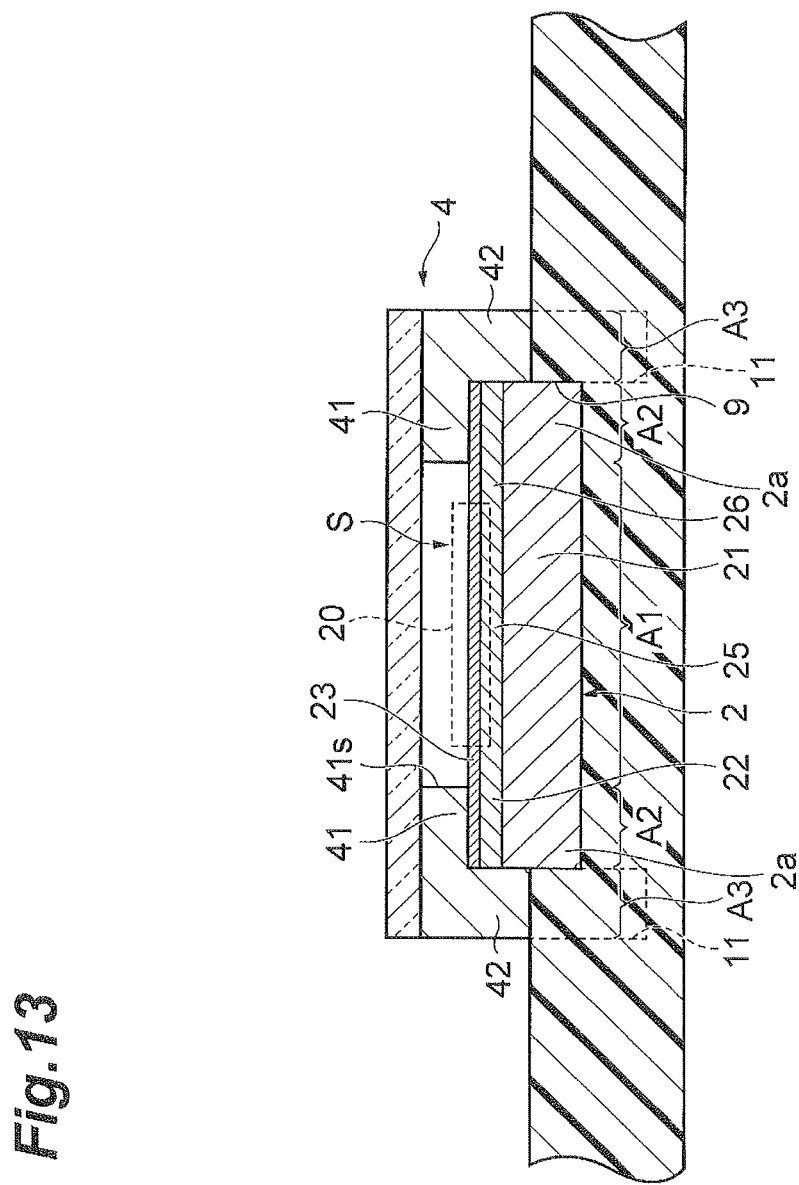
FIG. 13 is an enlarged sectional view of a modified example of the surface-enhanced Raman scattering unit of FIG. 8.

For example, as illustrated in FIG. 13, the measurement board 3 in the SERS unit 1B may be provided with only the depression 9 for containing a part of the SERS element 2 on the substrate 21 side and restraining the SERS element 2 from moving in directions perpendicular to the thickness direction of the substrate 21 without providing the depression 5 for containing the SERS element 2 and pressing member 4.

In this case, as illustrated in FIG. 14(a), guide grooves 15 for arranging the leg parts 42 of the pressing member 4 may further be provided in side faces of the depression 9 formed in the measurement board 3. This structure enables the leg parts 42 to be fitted into the fitting holes 11 easily and securely. In this case, the leg parts 42 can position the SERS element 2. As illustrated in FIG. 14(b), the depression 9 can position the SERS element 2 also when the guide grooves 15 are provided.

Figure 15:
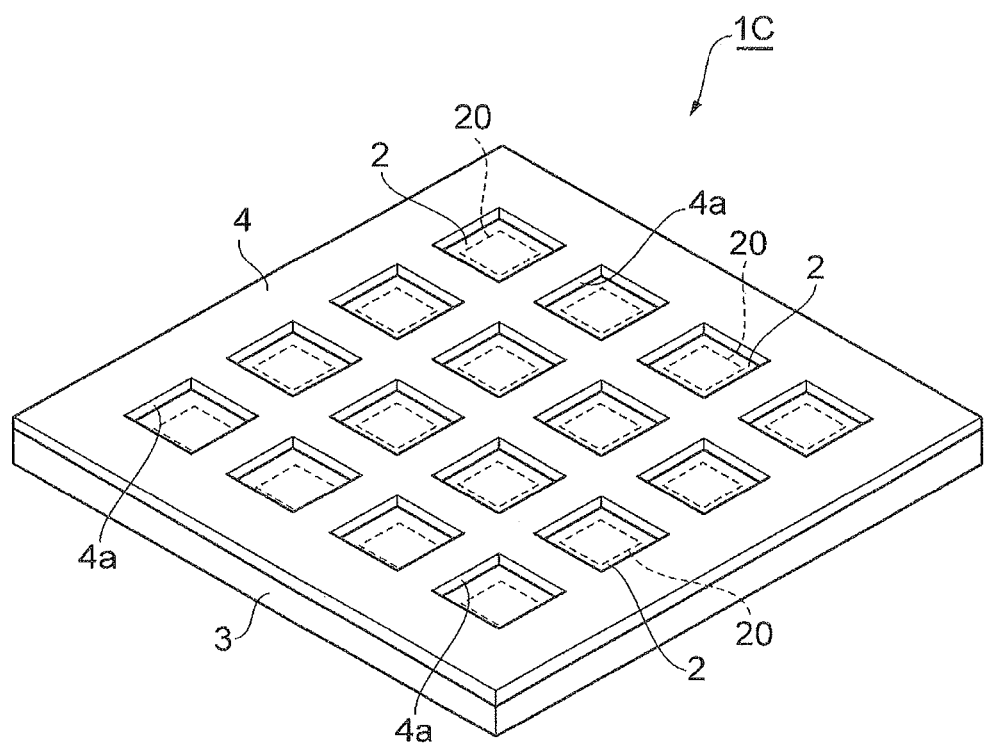
FIG. 15 is a perspective view of the surface-enhanced Raman scattering unit of another embodiment in accordance with one aspect of the present invention.

As illustrated in FIG. 15, a plurality of SERS elements 2 may be arranged on the measurement board 3, to which a pressing member 4 having a plurality of openings 4a corresponding to the respective optical function parts 20 (e.g., openings formed by inner side faces 41a of contact parts 41)

is attached. Thus constructed SERS unit 1C can efficiently perform Raman spectroscopic analysis for a plurality of samples.

The measurement board 3 may be made of low-melting glass, ceramics, and the like. The measurement board 3 can be formed integrally from low-melting glass as from a resin. From a ceramic, the measurement board 3 can be formed by firing, for example. Not only the above-mentioned materials and forms, but various materials and forms can also be employed for the structures of the SERS units 1A to 1C. For example, the ring shape is not limited to rectangular and circular rings but encompasses other ring shapes.

The region formed with the optical function part 20 is not limited to substantially the center region of the SERS element 2 (the area on the first region A1) when seen in the thickness direction of the substrate 21. That is, the optical function part 20 may further be formed in a region including the peripheral part 2a of the SERS element 2 (i.e., the area on the second region A2).

In the above-mentioned embodiment, the fine structure part 24 is formed on the surface layer of the molded layer 22 on the side opposite from the substrate 21. However, it does not limit the mode of forming the fine structure part 24. For example, the fine structure part 24 may be formed directly on the front face 21a of the substrate 21 without the molded layer 22 (support part 25) interposed therebetween. In this case, the conductor layer 23 can be formed on the front face 21a of the substrate 21 and the fine structure part 24, for example.

INDUSTRIAL APPLICABILITY

One aspect of the present invention can provide a surface-enhanced Raman scattering unit which can suppress adverse effects on the measurement without using a large amount of a sample, and a Raman spectroscopic analysis method using such a surface-enhanced Raman scattering unit.

REFERENCE SIGNS LIST 1A, 1B: SERS unit (surface-enhanced Raman scattering unit); 2: SERS element (surface-enhanced Raman scattering element); 2a: peripheral part; 3: measurement board; 3a: front face; 4: pressing member; 5: depression. (first depression); 6, 7: wall part; 8: hollowed part; 9: depression (second depression); 20: optical function part; 41: contact part; 41s: inner side face; 50: Raman spectroscopic analyzer; S: space.

The invention claimed is:
1. A surface-enhanced Raman scattering unit comprising:
 a measurement board used upon measurement;
 a surface-enhanced Raman scattering element, secured to the measurement board, having a substrate and an optical function part formed on the substrate, for generating surface-enhanced Raman scattering; and
 a pressing member, secured to the measurement board, having a ring-shaped contact part contacting with a peripheral part of the surface-enhanced Raman scattering element and pressing the surface-enhanced Raman scattering element toward the measurement board,
 the pressing member forms an opening surrounded by an inner side face extending along a thickness direction of the substrate; and
 when seen from the thickness direction of the substrate, the optical function part is exposed to outside of the pressing member via the opening.

2. A surface-enhanced Raman scattering unit according to claim 1, wherein the pressing member is mechanically secured to the measurement board.

3. A surface-enhanced Raman scattering unit according to claim 1, wherein the measurement board has a front face formed with a first depression; and
 wherein the surface-enhanced Raman scattering element and pressing member are contained within the first depression.

4. A surface-enhanced Raman scattering unit according to claim 3, wherein the pressing member has a top part substantially flush with the front face of the measurement board.

5. A surface-enhanced Raman scattering unit according to claim 1, wherein the contact part has an inner side face tilted in a tapering manner such that a space defined by the inner side face expands with distance from the surface-enhanced Raman scattering element.

6. A surface-enhanced Raman scattering unit according to claim 1, wherein the measurement board is provided with a second depression containing at least a part of the surface-enhanced Raman scattering element on the substrate side and restraining the surface-enhanced Raman scattering element from moving in a direction perpendicular to a thickness direction of the substrate.

7. A surface-enhanced Raman scattering unit according to claim 1, wherein the measurement board is integrally formed from a resin.

8. A surface-enhanced Raman scattering unit according to claim 7, wherein the measurement board is provided with a hollowed part so as to form a wall part extending in a direction perpendicular to a thickness direction of the measurement board.

9. A Raman spectroscopic analysis method comprising:
 a first step of preparing the surface-enhanced Raman scattering unit according to claim 1 and arranging a sample on the optical function part; and
 a second step, after the first step, of performing Raman spectroscopic analysis by setting the surface-enhanced Raman scattering unit to a Raman spectroscopic analyzer, irradiating the sample arranged on the optical function part with excitation light, and detecting Raman-scattered light derived from the sample.

* * * * *